United States Patent [19]

Gupta

[11] Patent Number: 4,660,412
[45] Date of Patent: Apr. 28, 1987

[54] THREE FLUID METHOD FOR NON-MERCURY INTRUSION POROSIMETRY

[75] Inventor: Krishna Gupta, Ithaca, N.Y.
[73] Assignee: Porous Materials Inc., Ithaca, N.Y.
[21] Appl. No.: 809,117
[22] Filed: Dec. 16, 1985
[51] Int. Cl.$^4$ ............................................. G01N 15/08
[52] U.S. Cl. ........................................................ 73/38
[58] Field of Search ................................. 73/38, 153

[56] References Cited

U.S. PATENT DOCUMENTS

| | | | |
|---|---|---|---|
| 2,293,488 | 8/1942 | Bays | 73/38 |
| 2,345,535 | 3/1944 | Horner | 73/38 |
| 2,829,515 | 4/1958 | Johnson | 73/38 |
| 2,886,964 | 5/1959 | Shapiro et al. | 73/38 |
| 3,158,020 | 11/1964 | Donaldson | 73/38 |
| 3,525,251 | 8/1970 | Marcu et al. | 73/38 |
| 3,882,714 | 5/1975 | Libal et al. | 73/38 |
| 4,170,128 | 10/1979 | Lowell | 73/38 |
| 4,203,317 | 5/1980 | Gupta | 73/38 |
| 4,272,983 | 6/1981 | Sisti et al. | 73/38 |

FOREIGN PATENT DOCUMENTS

| | | | |
|---|---|---|---|
| 70404 | 1/1983 | European Pat. Off. | 73/38 |
| 97035 | 6/1984 | Japan | 73/38 |

*Primary Examiner*—Jerry W. Myracle
*Assistant Examiner*—Hezron E. Williams
*Attorney, Agent, or Firm*—Barnard & Brown

[57] ABSTRACT

A three-fluid method of non-mercury liquid intrusion porosimetry. The sample to be tested and a quantity of non-wetting intrusion liquid other than mercury are introduced into a sealable, pressurizable chamber, the sample being above the intrusion liquid. The chamber is sealed and evacuated. An intermediate pressurizing liquid, such as mercury, is introduced into the chamber and pressurized by a primary pressurization fluid, such as alcohol or oil, so as to force the intrusion liquid into the pores of the sample. The volume of intermediate pressurization liquid introduced into the chamber is measured as the pressure is increased incrementally, to find the pore distribution of the sample.

13 Claims, 5 Drawing Figures

THREE FLUID METHOD FOR NON-MERCURY INTRUSION POROSIMETRY

BACKGROUND OF THE INVENTION

1. Field of the Invention

The present invention pertains to the field of porosimetry, or the measurement of the porosity of substances. More particularly, the invention relates to a liquid intrusion method for determining the porosity characteristics of a substance using a non-wetting liquid other than mercury.

2. Description of the Prior Art

The determination of porosity characteristics by intrusion of liquid mercury is a well known method. The method is used to determine the quantity of oil reserves in porous rock, in the fabrication of mineral raw materials to make ceramic or refractory bodies, and in many applications where the porosity of a substance must be ascertained.

Mercury is universally used as the intrusion liquid in commercial porosimetry since it does not wet most solids. That is, there is a repulsion of the liquid from the surface of the solid. Also, for a wide variety of solids, the "contact angle" of mercury is in the relatively narrow range of 135° to 142°, so it does not have to be measured for each sample. The contact angle is used with the pressure and the surface tension of the intrusion liquid to determine the size of the pores into which the liquid is intruding. These characteristics make mercury the most practical liquid for general characterization of the porosity and pore structure of porous materials, and the liquid of choice for virtually all porosimetry in the past.

The method of porosimetry used is the following: A sample of material is placed in a sample chamber, which is evacuated to eliminate the air from the pores of the sample. The sample is then immersed in a non-wetting liquid, almost always mercury, as noted above. The mercury is then forced into the pores of the sample under pressure. By gradually increasing the pressure of a pressurization fluid (usually alcohol or oil) on the mercury supply and measuring the decrease in volume of the mercury surrounding the sample, the porosity characteristics of the material can be determined. The volume of mercury is determined by using a column of mercury as a reservoir, in which the height of the column can be accurately measured. The column is called a "penetrometer".

Problems often arise from using porosimeters of the mercury intrusion type to measure very small pores. Mercury has a relatively high surface tension, as well as a large non-wetting contact angle with most solids. Thus, very high pressures are needed to force mercury into the fine pores that are present in many materials, and the sample is sometimes crushed as a result. Commercial porosimeters typically operate at pressures up to 60,000 psia, which will intrude mercury into pores as small as 35 Angstroms in diameter. The use of non-wetting liquids other than mercury in porosimetry is potentially advantageous in that lower pressures can be used, thereby reducing the risk of crushing samples during testing.

In addition to the information obtained as to pore structure, it is sometimes desirable to test a material with a non-wetting liquid other than mercury that may actually be involved in the application or end use of the material, to obtain direct information about the solid-liquid interaction of interest. For example, the method of the invention has been used in porosimetry studies of TFE(Teflon TM)-bonded fuel cell electrodes in which the intrusion liquid is aqueous KOH, the electrolyte actually used in the operation of the electrodes. In this case the use of aqueous KOH rather than mercury as the intrusion liquid reduces the pressures required by a factor of 13.

In principle, any non-wetting liquid could be used for porosimetry, provided that the penetration volume can be measured accurately. In practice, this is difficult. The extremely high pressures involved, especially in mercury porosimetry, preclude the use of visual penetrometers, since the glass used to contain the columns of fluid could burst. The more reliable and accurate penetrometers in current use are based on one of two measurement techniques: the mercury in the penetrometer column may be used as part of an electrical circuit in which an electrical characteristic (such as resistance, inductance or capacitance) varies with the mercury level; or through the use of a magnetic float on top of the mercury column, using means for detecting the position of the float magnetically (see K. Gupta, U.S. Pat. No. 4,203,317). These techniques work well with mercury because of its electrical properties, for the first method, or its high density, for the second. It is unlikely that any other liquid of potential interest for porosimetry would work with a penetrometer based on one of these prevalent methods. Thus, simply substituting aqueous KOH, for example, for mercury in a conventional porosimeter would not be possible. At the same time, it would not be economical for most users to have a special porosimeter reserved for use solely with a liquid other than mercury, even if such could be built.

It is thus an object of the invention to provide a method for non-mercury porosimetry which can be performed using conventional porosimeters.

It is a further object of the invention to provide a method for non-mercury porosimetry which can be performed using porosimeters designed for mercury intrusion, without losing the capability of performing mercury porosimetry using the same equipment.

SUMMARY OF THE INVENTION

The method of the invention begins with a conventional porosimeter arrangement, which includes a sealable chamber for containing a sample of a porous material, means for evacuating the chamber, a penetrometer for measuring the volume of mercury intruded into the sample, means for pressurizing the mercury using a pressurization fluid, and appropriate means for connecting the penetrometer to the sample chamber.

This conventional arrangement might be termed a "two-fluid porosimeter", since it uses a pressurization fluid and fluid (liquid) mercury. The pressurization fluid must be immiscible with the mercury, and less dense. If the float method of determining the column height in the penetrometer is used, then the pressurization fluid must also be less dense than the float. Usually, oil or alcohol is used as pressurization fluid, since it is easier to generate high pressures with a liquid than with a gas, but air or another gas could also be used. Since pressurization fluid plays no part in the novelty of the invention, it is merely noted that the fluid must meet the above qualifications, and will be referred to as a "fluid" with no further detail herein.

The mercury, which is pressurized by the pressurization fluid, is used in the conventional porosimetry method as the intrusion liquid. In the method of the invention, it becomes an intermediate pressurization liquid, pressurizing a non-mercury intrusion liquid. Thus, the method of the invention may be termed "free fluid porosimetry".

It will be understood that, while the intermediate liquid is referred to as "mercury" in the following description, since mercury is in fact what is currently used in porosimeters as discussed above, in fact some other intermediate liquid may be used if it meets the following requirements: it must be immiscible with the pressurization fluid and the intrusion liquid; it must be more dense than the pressurization fluid and the intrusion liquid; the interface between the intermediate liquid and the pressurizing fluid must be detectable—either visually, in the case of a transparent penetrometer, or if using the float method in the penetrometer, the intermediate liquid must be denser than the float, or if using one of the electrical methods, it must have suitable electrical characteristics; it must be incompressible; and it must be non-volatile at the temperatures used. For ease of reference, the intermediate liquid will be referred to herein as simply "mercury".

The sample chamber preferably has means for supporting a sample above the bottom of the chamber, and a port or ports for evacuating the chamber and introducing mercury into the chamber. The mercury introduction port is preferably located below the supporting means, but may be combined with the evacuation port.

The sample to be tested is placed in the chamber, preferably supported above the bottom of the chamber, for reasons which will become apparent. If the intrusion liquid is non-volatile (i.e. will not vaporize at low pressure and at the temperature being used) then a sufficient volume of intrusion liquid to ensure that the sample will always be surrounded by the liquid during the intrusion phase of the test, even after all of the pores in the sample are filled, is placed in the sample chamber. The chamber is then sealed and evacuated. If the intrusion liquid is volatile, then these steps are reversed, and the chamber is sealed and evacuated, then the liquid is introduced into the evacuated chamber.

Preferably, the sample is not contacted by the intrusion liquid until after the chamber has been evacuated and the pressurization phase (below) has begun. If the sample is in contact with the liquid during the evacuation phase, then the pores communicating with those surfaces of the sample which are in contact with the liquid may not be evacuated completely, leaving gas in the pores to resist intrusion.

The pressurization phase begins as mercury is added from a reservoir (the entry point to the chamber being preferably below the sample) so that the chamber is filled. The mercury is then pressurized, and the additional amount of mercury entering the chamber at each pressure is measured with the penetrometer. The additional volume of entering mercury is equal to the volume of intrusion liquid entering the sample.

The porosimetry method of the invention can use any incompressible non-wetting liquid as an intrusion liquid which has a specific gravity lower than 13.6, the specific gravity of mercury (if mercury is the intermediate liquid, as discussed above). If a molten solid is used as the intrusion liquid, then it must have a melting point lower than the boiling point of mercury to insure accurate measurements and the sample chamber should be heated to keep the intrusion liquid from solidifying.

DESCRIPTION OF THE PREFERRED EMBODIMENT

Figure 1:
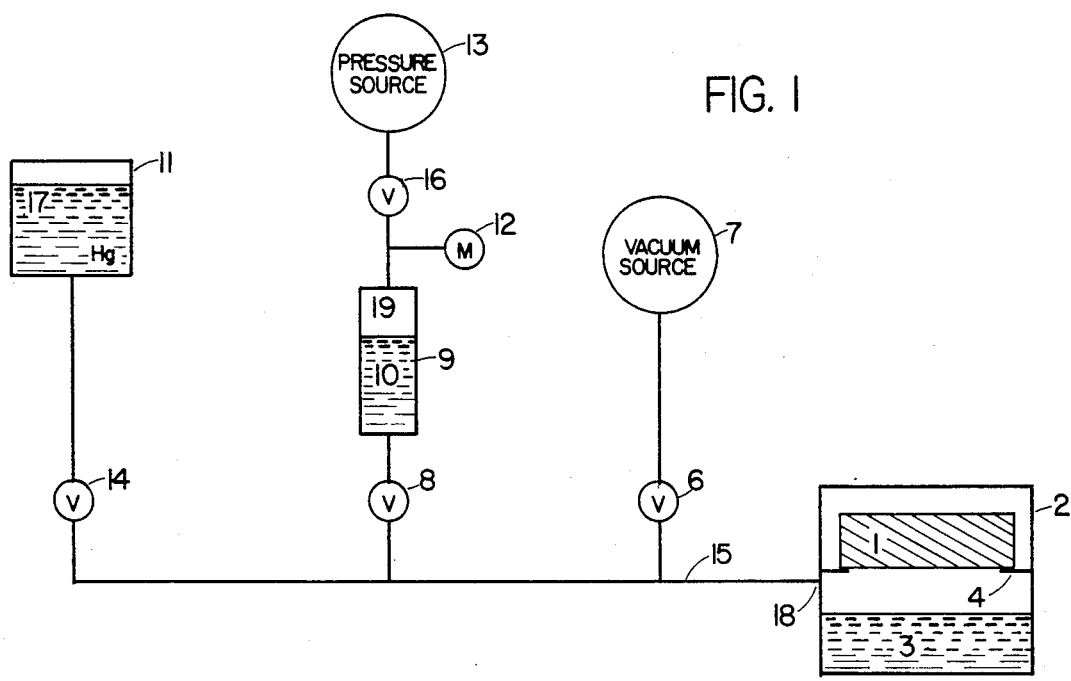
FIG. 1 schematically depicts a porosimeter which could be used with the method of the invention.

Reference to FIG. 1 will aid in an explanation of the method of the invention, in its simplest form, using a conventional porosimeter and non-volatile intrusion liquid.

A sample (1) of a material whose porosity characteristics are to be determined is placed in a sample chamber (2). The sample chamber (2) is connected to a vacuum source (7) through a conduit (15), and valve (6). The sample chamber (2) is also connected through conduit (15) and valve (14) to a mercury reservoir (11) which is filled with mercury (17). It is preferred that a separate penetrometer (9) and valve (8) be provided, as shown, to allow more accurate measurement of the level of mercury (10), for reasons which will become obvious. It will be understood, however, that the functions of penetrometer (9) and reservoir (11) may be combined into one single calibrated reservoir, possibly at some loss in accuracy. The reservoir (11) can be located above the penetrometer (9) so that the penetrometer may gravity fill with mercury from the reservoir, as described below.

The exact means of measurement of mercury level is not important to the invention, and may include visual observation through a transparent tube, detection of electrical characteristics, or magnetic detection of a float. The mercury in the penetrometer may be pressurized by introduction of a fluid (19) under pressure. The pressurization fluid is preferably a liquid such as alcohol or oil, since it is easier to generate high pressures with such liquids. However, if desired the fluid could be a gas such as air. The fluid is pressurized by any convenient method known to the art such as a pump or a source of pressurized gas such as a storage tank. The type of pressurization fluid which is chosen, within the limitations noted above, and the method by which it is pressurized, forms no part of the invention, and is merely shown as a "pressure source." A meter (12) is provided to allow the applied pressure to be measured.

The method of the invention for non-volatile intrusion liquids proceeds as follows: First, the intrusion liquid (3) is placed in the sample chamber (2). The quantity of intrusion liquid must be adequate to ensure that the sample (1) will remain surrounded by intrusion liquid throughout the intrusion phase of the test. This could range from slightly more than the total pore volume of the sample, if the chamber is only slightly larger than the sample, to much more than the pore volume, depending on the sample and the chamber design.

It is preferred to support the sample (1) above the bottom of the chamber (2), so that gas can be removed from all of the pores in the sample before intrusion, and so that the intrusion liquid can reach all of the pores during pressurization. If the sample were in contact with the intrusion liquid during evacuation, it is possible that all of the pores in the sample might not be fully evacuated. If the sample rested on the bottom of the sample chamber, it is also possible that many pores might be blocked off from the intrusion liquid by the mercury entering the chamber. In a worst case, if the sample was denser than both the intrusion liquid and the mercury (i.e. sinks to bottom of chamber), and if the sample chamber was deep enough, the sample could wind up entirely surrounded by mercury, and never contact the intrusion liquid at all.

The intrusion liquid used will depend upon the application. Appropriate intrusion liquids are those with specific gravities less than that of mercury, so that the mercury introduced into the chamber will sink below the intrusion liquid. Since the specific gravity of mercury is a very high 13.6, this is not a significant limitation. The intrusion liquid must not wet the sample, otherwise the pores would fill by capillary action without applied pressure.

Figure 4:
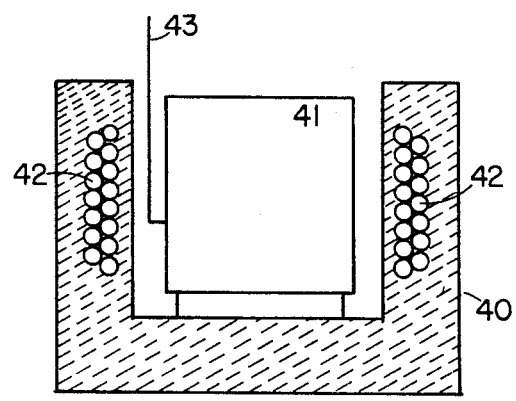
FIG. 4 shows an alternate design of the sample chamber, for intrusion liquids which must be kept at high temperatures, such as molten solids.

If desired (FIG. 4) the sample chamber (41) may be surrounded by a furnace or heater, here shown as a suitably shaped chamber (40) of refractory material with heating coils (42) embedded. The evacuation and pressurization conduit (43) leads out of the furnace to the vacuum and pressure sources. Other arrangements of the furnace, chamber and conduit are possible within the teachings of the invention. If such a furnace is provided, a melted solid can be used as an intrusion liquid, melted by the heat of the furnace. The solid is placed in the sample chamber or cell and heated until it is molten. At that point the method proceeds as previously described. Obviously, the sample must be able to withstand the elevated temperature, and the molten solid should have a melting point lower than the boiling point of the mercury to be introduced into the cell (41) as the intermediate liquid.

Liquids with a moderate volatility, such as aqueous potassium hydroxide (KOH) have been successfully used with the method of the invention, so long as the user is careful that the chamber is not evacuated to such a low pressure that the liquid evaporates quickly at room temperature. Alternatively, volatile liquids can be used in the alternate embodiment described below.

Once the desired amount of intrusion liquid (3) is added to the chamber (2), the sample (1) is added. As discussed above, the sample is preferably supported (4) above the intrusion liquid, so that gas can be removed from the pores within the sample before the intrusion of liquid. This also insures that it is the intrusion liquid, and not the mercury intermediate liquid, which penetrates the sample pores when pressure is applied. If the sample has a specific gravity low enough that it may float upon the intrusion liquid, it may simply be placed into the chamber and allowed to float. Preferably, however, support means (4) are provided to support the sample (1) above the liquid (3).

The sample having been placed inside, the chamber is sealed. Valve (6) is opened, and the vacuum source (7) is allowed to evacuate the chamber (2) through a conduit (15). As noted above, if the liquid is volatile at the temperature being used, the chamber should not be evacuated to so low a pressure that significant liquid (3) evaporates during evacuation. The chamber having been evacuated, valve (6) is closed.

The sample is now in a chamber with the intrusion liquid and a vacuum (or near-vacuum). Valves (8) and (14) are opened, and mercury (17) is fed into the chamber (2) and the penetrometer (9). Because of its high specific gravity, the mercury sinks to the bottom of the sample chamber (2). The intrusion liquid (3) floats on top of the mercury and surrounds the sample (1) resting on its supports (4). As shown, it is preferable (although not required) to introduce the mercury through a port (18) in the side of the sample chamber (2), below the sample (1). In this way, the introduced mercury intermediate liquid does not flow over the sample.

When the chamber and penetrometer have filled, the valve (14) to the reservoir (11) is closed.

At this time, the pressurization and intrusion phase of the porosimetry testing begins. The pressure source (13) is used to pressurize the mercury in progressive and incremental steps. The pressure is raised to a specific point with the pressure control (16), and read on the meter (12). At each chosen pressure point, the amount of mercury entering the chamber is measured by measuring the drop in mercury level in the penetrometer (9). The volume of mercury introduced from the penetrometer at a given pressure is equal to the volume of intrusion liquid forced into the pores of the sample at that pressure, and the pore volume distribution may then be computed by well-known techniques, since the pressure and the size of the pore into which the liquid intrudes at that pressure are inversely related in a fashion which is well-known to the art, using the formula:

$$Pg - Pl = 2o \cos O/R$$

where Pl is the pressure of the intrusion liquid, Pg is the pressure of the gas within the pores (Pg is almost zero if the pores are evacuated), o is the surface tension, O is the contact angle, and R is the pore radius.

Figure 2:
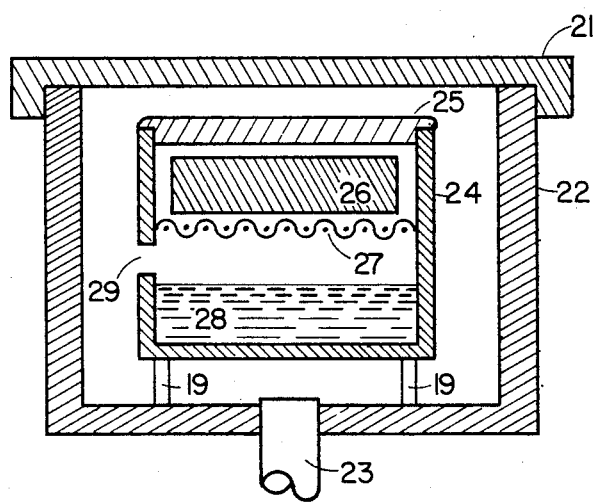
FIG. 2 shows a detail of a modified sample chamber for use with the invention.

FIG. 2 shows details of a sample chamber which is especially suited to the method of the invention. Inside the chamber (22), which has a removable lid (21) to allow access to the inside of the chamber, is a sample cell (24), which also has a removable lid (25). The cell (24) has a hole (29) in its side, approximately half-way between the top and bottom of the cell. The cell also has supports for the sample, located at approximately one-third of the distance from the top of the cell. In this case, the support is shown as a screen (27), which is suitable for a variety of types of samples. It will be understood that other types of supports are possible within the teachings of the invention. The support (27) is preferably located above the hole (29), so that mercury entering the cell from the hole will not flow over the sample (26). The cell (24) is supported above the bottom of the chamber (22) by some form of supports (19) such as the legs shown here. This allows a conduit (23) for evacuation and pressurization to enter the chamber from below.

The use, the chamber of FIG. 2 is used as follows: The intrusion liquid (28) is put in the cell (24), filling the cell to a point approximately one-third of the distance from the bottom of the cell. It would, of course, be possible to fill the cell up to the level of hole (29), if desired. The sample (26) is placed in the cell (24), and lids (25) and (21) put on the cell and the chamber, respectively. The chamber is now evacuated and pressurized as described above. The cell acts within the chamber to minimize contamination of the porosimeter by particles of the sample, or the intrusion liquid, or vapor from the intrusion liquid, and also minimizes the volume of intrusion liquid required. In addition, the sample cell may be used with conventional porosimeters, to allow the method of the invention where it would not be desirable to actually fill the sample chamber with intrusion liquid, for example where the port for evacuation and/or pressurization is located in the bottom of the chamber, as shown here. In such a case, it would obviously be impossible to evacuate the cell, if the evacuation port were to be submerged under intrusion liquid.

Figure 3A:
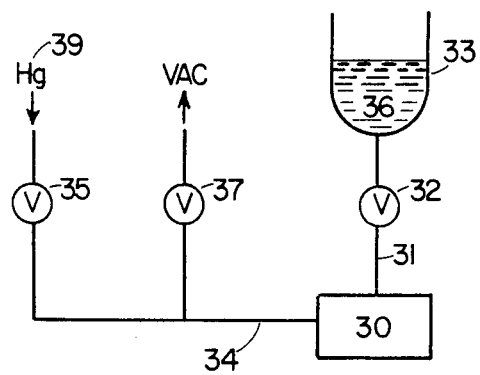
FIGS. 3a and 3b show a variation on the porosimeter design adapted for use with volatile intrusion liquids.
Figure 3B:
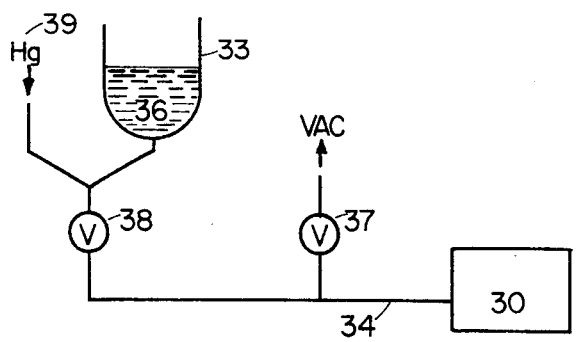

FIGS. 3A and 3B show a modification of the porosimeter, especially suited for use with the method of the invention when testing with intrusion liquids which are volatile (i.e. have significant vapor pressure at the temperature being used). As noted above, for volatile liquids it is preferred to evacuate the chamber first, then introduce the intrusion liquid. If done in the order described above for non-volatile liquids, the intrusion liquid will tend to evaporate and be drawn into the vacuum system and it will be impossible to properly evacuate the pores in the material (noncondensible gases must be removed).

In order to accomplish this, the system must be modified to allow introduction of the intrusion liquid (36) into the chamber (30) after it has been evacuated. This may be done by adding another inlet to the sample chamber (30), and adding a conduit (31) leading to a reservoir (33) through an appropriate valve (32), as shown in FIG. 3A. Alternatively, as shown in FIG. 3B, it is possible to introduce the intrusion liquid through the same inlet (34) as that used to evacuate the chamber and introduce the mercury, by replacing valves (32) and (35) with an appropriate two-way valve (38) selecting between the reservoir of intrusion liquid (33) and the pressurization source (39).

When a volatile intrusion liquid is admitted to an evacuated sample chamber, some of the liquid will vaporize to establish its equilibrium vapor pressure in the gas phase. When the mercury is then admitted, the volume of the gas phase in the sample chamber is reduced, so some vapor must condense to maintain the equilibrium vapor pressure within the pores. This continues as the vapor volume decreases with increased applied pressure, until all the pores are filled with intrusion liquid.

Although particular embodiments of the invention are described herein, it is to be understood that various changes, substitutions, and alterations can be made in the steps of the method, in the components of the apparatus, and in the combinations of the components without departing from the spirit and scope of the present invention, as defined in the appended claims, which solely define the scope of the invention. Accordingly,

I claim:

1. The method of evaluating the porosity characteristics of a sample of material with respect to an intrusion liquid other than mercury, using a porosimeter of the type having a sealable sample-holding chamber; a reservoir of an intermediate pressurization liquid; means for measuring the quantity of intermediate pressurization liquid in the reservoir; a source of pressurizing fluid connected to the reservoir of intermediate pressurization liquid, whereby the reservoir may be pressurized by introduction of the pressurization fluid under pressure; means for measuring the pressure; means for evacuating the sample-holding chamber; and means for connecting the intermediate pressurization liquid reservoir to the sample chamber, whereby intermediate pressurization liquid under pressure may be introduced into the sample chamber; the improved method comprising the steps of:
   a. putting a volume of the intrusion liquid having a specific gravity lower than the specific gravity of the intermediate pressurizing liquid at least equal to the expected pore volume of the sample in a sealable sample chamber;
   b. placing the sample to be tested in the sample chamber above the intrusion liquid;
   c. sealing the sample chamber;
   d. evacuating the sample chamber;
   e. introducing intermediate pressurization liquid into the sample chamber from the reservoir whereby the volume of the chamber is completely filled with the sample, intrusion liquid, and intermediate pressurization liquid;
   f. introducing pressurizing fluid into the reservoir in an incremental and progressive manner, pressurizing the intermediate pressurization liquid in the reservoir, forcing additional intermediate pressurization liquid into the sample chamber under pressure, whereby the intrusion liquid is forced into pores of the sample;
   g. measuring the quantity of intermediate pressurization liquid in the reservoir at each pressure, whereby the amount of intermediate pressurization liquid entering the sample chamber, and therefore the amount of intrusion liquid entering the pores of the sample, may be determined at each pressure applied.

2. The method of claim 1 wherein the sample is supported above the intrusion liquid by support means located in the sample chamber.

3. The method of claim 1 in which the sample chamber further comprises separate sample cell means located within the sample chamber for containing the sample and the intrusion liquid.

4. The method of claim 3 in which the sample cell means comprises:
   a. a hollow enclosed body having removable access to the inside thereof, said body being at least large enough to contain the sample and the intrusion liquid;
   b. support means for supporting the sample, located inside the body such that the sample, when placed on the support means, is supported above the intrusion liquid;
   c. the body having a hole communicating between the inside and outside thereof, located below the support means and above the level of the intrusion liquid, through which the cell may be evacuated of gas and intermediate pressurization liquid may enter the cell.

5. The method of claim 1 wherein the intermediate pressurization liquid is introduced at a level in the sample chamber below the sample.

6. The method of claim 1 wherein the intrusion liquid is a molten solid, having a melting point below the boiling point of the intermediate pressurization liquid.

7. The method of claim 6, in which the sample chamber is surrounded by a heater to maintain the intrusion liquid in a molten state.

8. The method of claim 1 in which the intrusion liquid is volatile, and step "a" is performed after step "d", such that the chamber with sample therein is first evacuated, then the intrusion liquid is introduced.

9. The method of claim 1 in which the intermediate pressurization fluid is mercury.

10. The method of claim 1 in which the pressurizing fluid is alcohol.

11. The method of claim 1 in which the pressurizing fluid is oil.

12. The method of claim 1 in which the pressurizing fluid is a gas.

13. The method of claim 12 in which the pressurizing fluid is air.

* * * * *